US007721456B2

(12) United States Patent
Marichi Rodriguez et al.

(10) Patent No.: US 7,721,456 B2
(45) Date of Patent: May 25, 2010

(54) MEASURING APPARATUS FOR THE PROGRAMMING AND WELDING OF ADJUSTABLE BRACKETS

(76) Inventors: Francisco Javier Marichi Rodriguez, Calle Sur 132 No. 132-1, Col. Las Americas, Mexico City (MX) CP 01120; Roberto Ruiz Diaz, Calle Ocaso No. 101-202, Col. Insurgentes Cuicuilco, Mexico City (MX) CP 04530

( * ) Notice: Subject to any disclaimer, the term of this patent is extended or adjusted under 35 U.S.C. 154(b) by 48 days.

(21) Appl. No.: 12/158,675

(22) PCT Filed: Dec. 20, 2006

(86) PCT No.: PCT/MX2006/000150

§ 371 (c)(1),
(2), (4) Date: Sep. 24, 2008

(87) PCT Pub. No.: WO2007/073143

PCT Pub. Date: Jun. 28, 2007

(65) Prior Publication Data

US 2009/0136892 A1    May 28, 2009

(30) Foreign Application Priority Data

Dec. 21, 2005    (MX) .................. PA/A/2005/014182

(51) Int. Cl.
*A61C 19/04* (2006.01)
(52) U.S. Cl. ............................. 33/513; 433/3
(58) Field of Classification Search .................. 33/511, 33/513, 514; 433/3
See application file for complete search history.

(56) References Cited

U.S. PATENT DOCUMENTS 2,959,857 A    11/1960  Stoll (Continued)

FOREIGN PATENT DOCUMENTS

EP    0 285 418 A2    10/1988

(Continued)

*Primary Examiner*—G. Bradley Bennett
(74) *Attorney, Agent, or Firm*—Reinhart Boerner Van Deuren P.C.

(57) ABSTRACT

This invention refers to a MEASURING APPARATUS FOR THE PROGRAMMING AND WELDING OF ADJUSTABLE BRACKETS permitting the electrical spot welding with a great accuracy of the elements of an adjustable bracket, in this manner being able to adjust or to program the information that the orthodontist wants to incorporate in the bracket in regard to inclination, angulation and rotation. In order to achieve this aim I developed two attachments: THE POSITION MEASURING ACCESSORY and the WELDING ACCESSORY.

Figure 1:
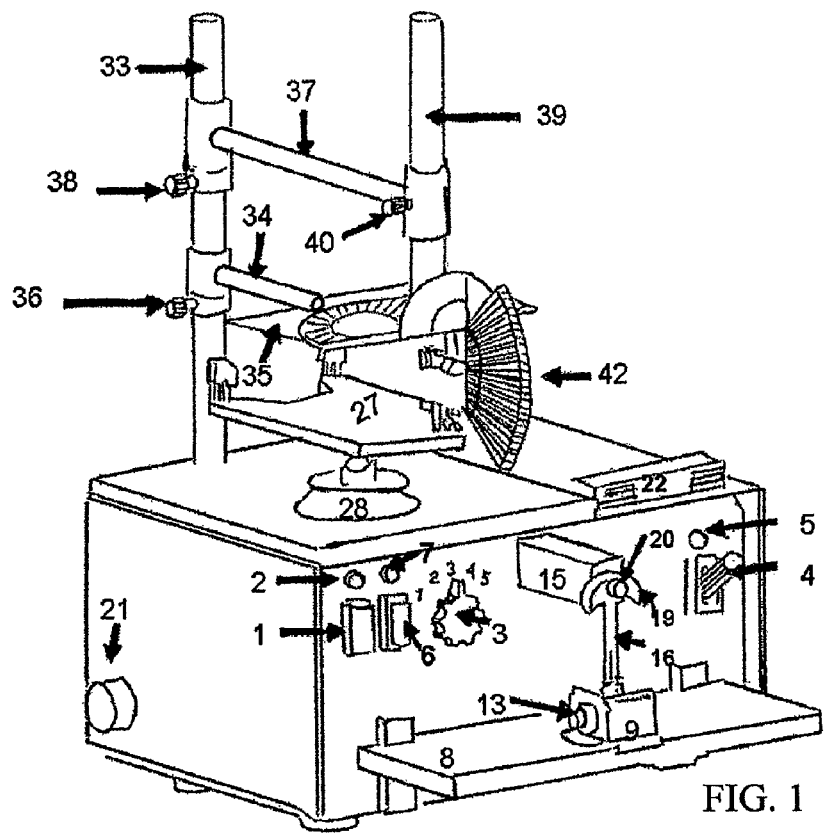

THE POSITION MEASURING ACCESSORY has the function of recording or measuring accurately the dental position as for inclination, angulation and rotation on dental casts. This measurement is performed by means of a template system that allows the recording a tooth position in relation to its osseous basis and the occlusal plane.

THE WELDING ACCESSORY has the innovation of allowing the accurate welding of the adjustable bracket elements (base and body), being able to adjust or program (in the three space planes) the information of inclination, angulation and rotation that the orthodontist wants to incorporate in the bracket by means of three fine graduation systems.

14 Claims, 14 Drawing Sheets

U.S. PATENT DOCUMENTS

| | | | |
|---|---|---|---|
| 3,439,421 A | | 4/1969 | Perkowski |
| 3,452,177 A | | 6/1969 | Davis et al. |
| 3,908,271 A | * | 9/1975 | Derda et al. .................. 433/58 |
| 4,083,114 A | | 4/1978 | Acevedo |
| 4,209,906 A | | 7/1980 | Fujita et al. |
| 4,256,455 A | | 3/1981 | Foerster et al. |
| 5,160,262 A | * | 11/1992 | Alpern et al. .................. 433/58 |
| 5,219,282 A | | 6/1993 | Lavin |
| 5,711,666 A | | 1/1998 | Hanson |
| 6,371,760 B1 | | 4/2002 | Zavilenski et al. |
| 2002/0098460 A1 | | 7/2002 | Farzin-Nia et al. |
| 2005/0003324 A1 | | 1/2005 | Reising |
| 2007/0134619 A1 | * | 6/2007 | Lee .............................. 433/57 |
| 2008/0261169 A1 | * | 10/2008 | Gutman et al. ................ 433/69 |
| 2009/0305185 A1 | * | 12/2009 | Lauren ......................... 433/29 |
| 2009/0310852 A1 | * | 12/2009 | Cheng et al. ................ 382/154 |

FOREIGN PATENT DOCUMENTS

| | | |
|---|---|---|
| EP | 0 702 939 A2 | 3/1996 |
| EP | 0 780 101 A2 | 6/1997 |
| EP | 1723927 A1 | 11/2006 |
| WO | WO 99/40871 A1 | 8/1999 |
| WO | WO 2004052229 A2 | 6/2004 |
| WO | WO 2005067810 A1 | 7/2005 |

\* cited by examiner

MEASURING APPARATUS FOR THE PROGRAMMING AND WELDING OF ADJUSTABLE BRACKETS

CROSS-REFERENCE TO RELATED PATENT APPLICATIONS

This patent application is the National Stage of International Application No. PCT/MX2006/000150, filed Dec. 20, 2006, that claims priority to Mexican Application No. PA/a/ 2005/014182, filed Dec. 21, 2005, the entire teachings and disclosure of which are incorporated herein by reference thereto.

BACKGROUND TO THE INVENTION

Nowadays, the welding machines used by orthodontists allow to perform the electrical spot welding of the attachments used in orthodontic treatments, for instance lingual attachments to bands or brackets to bands. The electrical spot welding performed chair-side presently lacks the precision required to weld an adjustable bracket providing accurate programming or prescription information.

With the aim of solving these and other drawbacks, I thought of developing the present appliance I am seeking to protect by means of this request, since it is an invention which allows the orthodontist to record the dental position in the three space planes on dental casts; and to be able to weld adjustable brackets incorporating the desired programming of inclination, angulation and rotation, thus having individualization for each treatment.

THE MEASURING APPARATUS FOR THE PROGRAMMING AND WELDING OF ADJUSTABLE BRACKETS includes two main sections:

1. Position Measuring Accessory

It is an innovative precision system for measuring in dental casts the accurate dental position of the teeth in regard to inclination, angulation and rotation.

2. Welding Accessory

It belongs to the electrical welding or electrical spot welding section; it has the innovation of including three graduating systems (in the three space planes) for the accurate electrical spot welding of the two elements of the adjustable bracket, according to the information of inclination, angulation and rotation that the orthodontist wants to program.

DESCRIPTION OF THE INVENTION

THE MEASURING APPARATUS FOR THE PROGRAMMING AND WELDING OF ADJUSTABLE BRACKETS is manufactured in a metal chassis. With regard to the electrical principles, its functioning is similar to that of available orthodontic welding machines, but in regard to the operative aspect it is completely different, having an innovation consisting in a system of accessories which allows the precision electrical spot welding for adjustable brackets (THE WELDING ACCESSORY) as well as a graduation system to determine the accurate dental position in dental casts (POSITION MEASURING ACCESSORY).

A BRIEF DESCRIPTION OF FIGURES

FIG. 1. It shows a view of the appliance in perspective.

Figure 2:
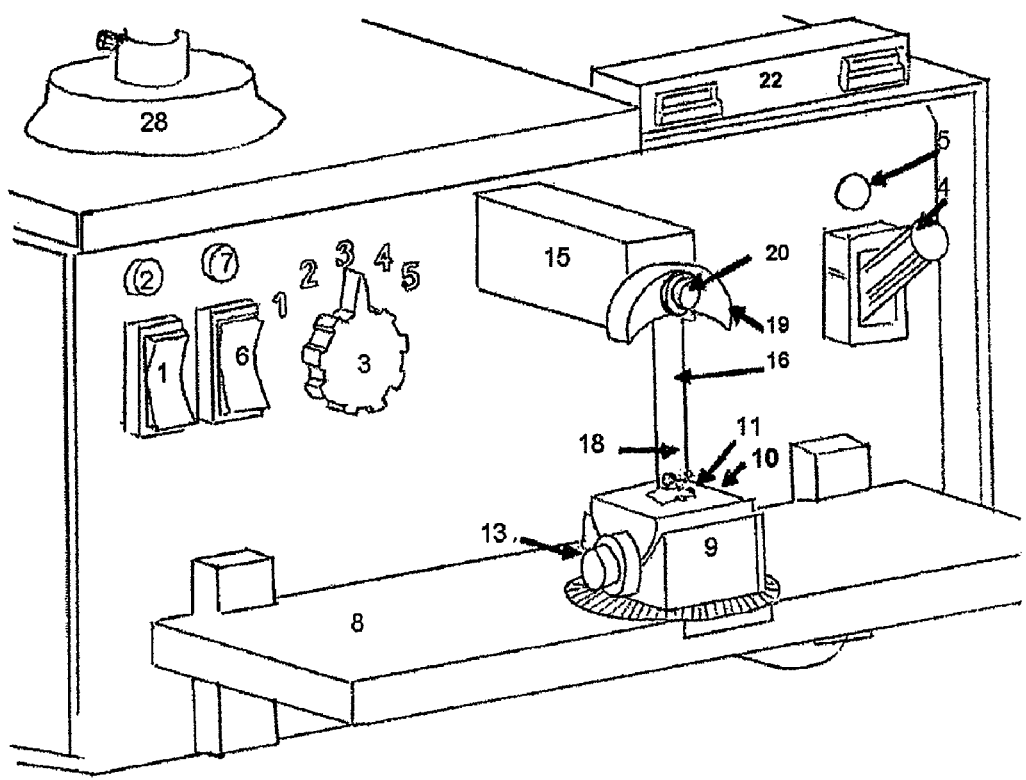

FIG. 2. It shows a view of the welding section of the appliance.

Figure 3:
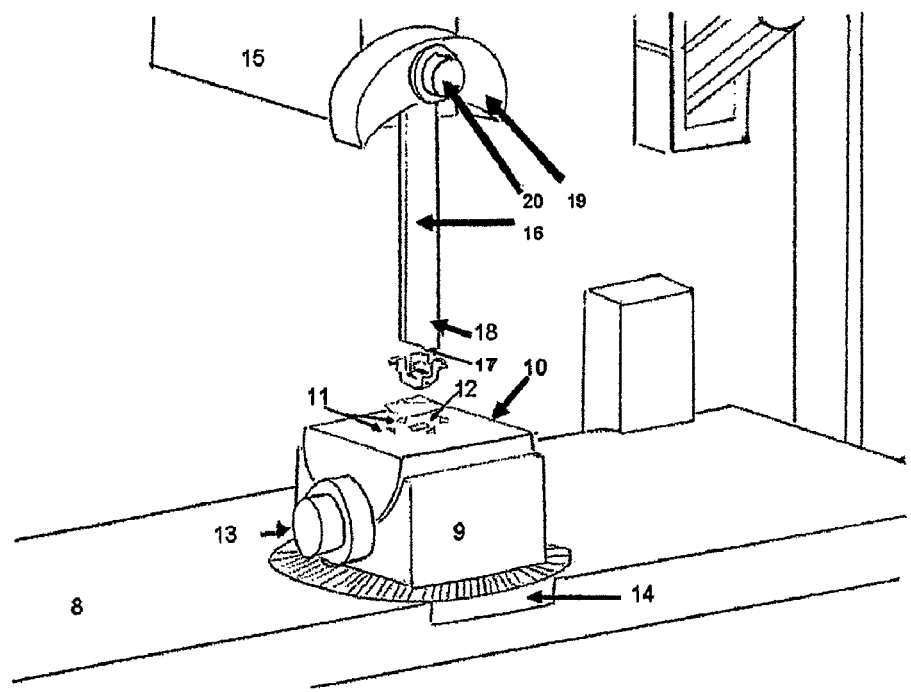

FIG. 3. It shows a view of the welding accessory.

Figure 4:
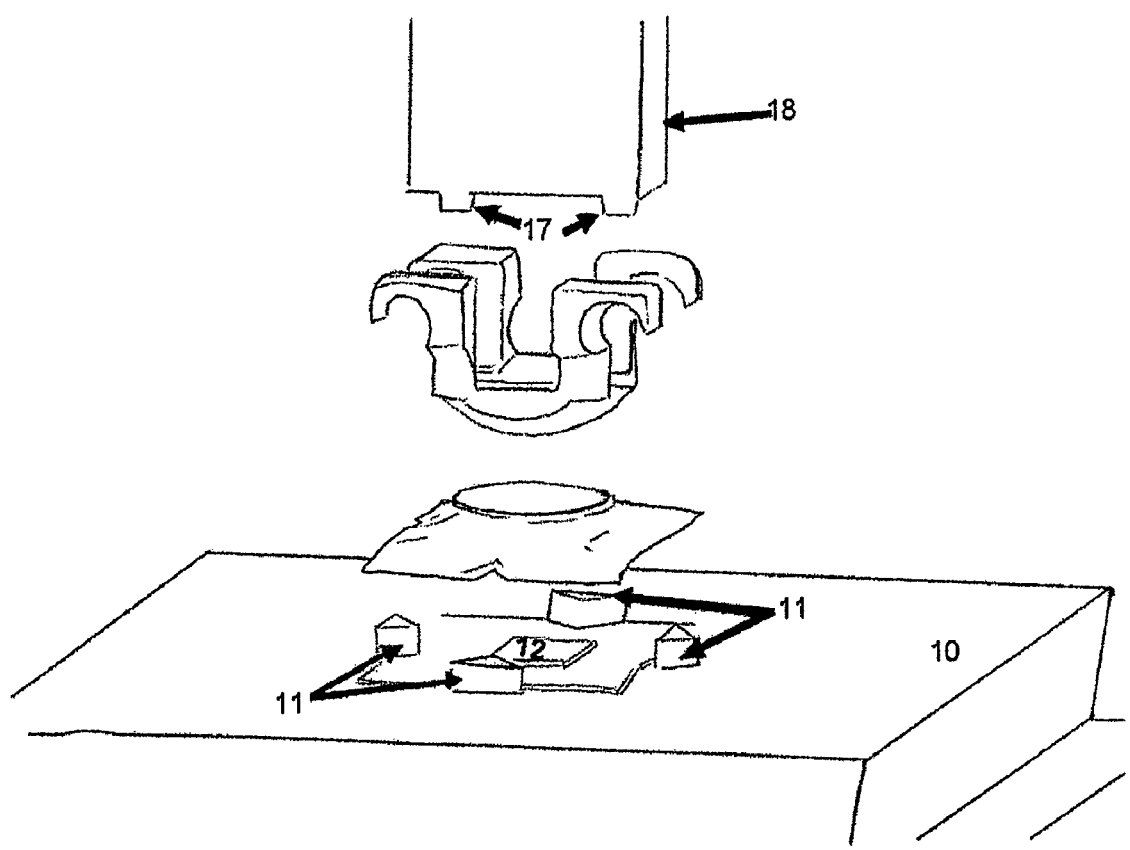

FIG. 4. It shows a close-up view of the welding table.

Figure 5:
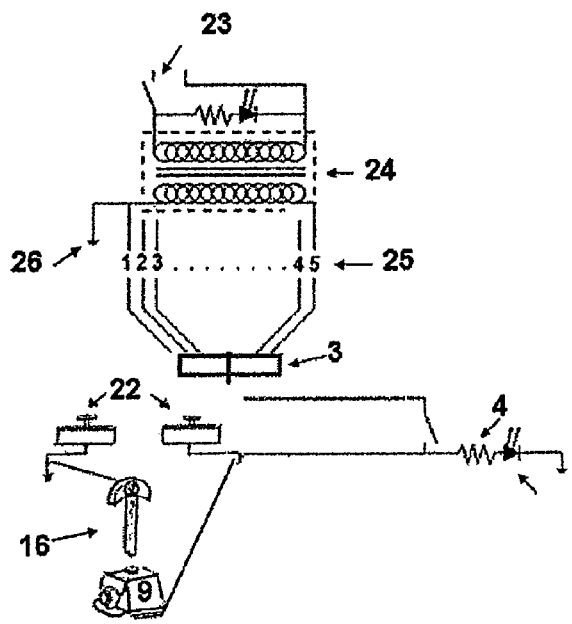

FIG. 5. It shows a diagram of the welding section.

Figure 6:
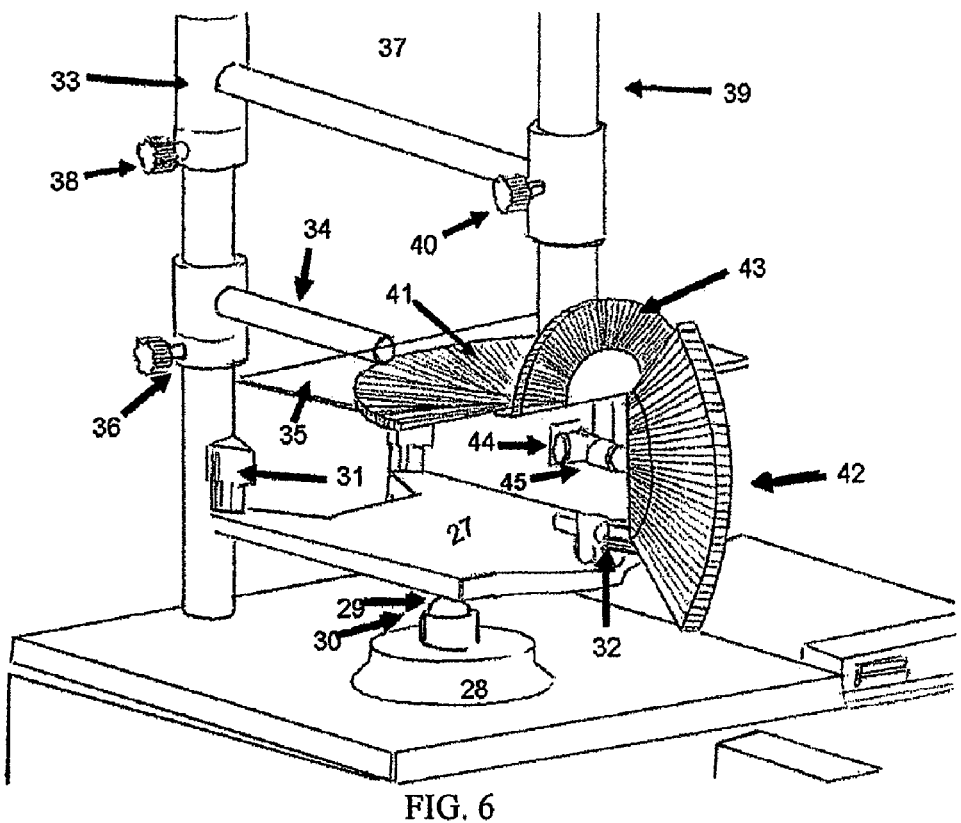

FIG. 6. It shows a view of the precision position measuring accessory.

Figure 7:
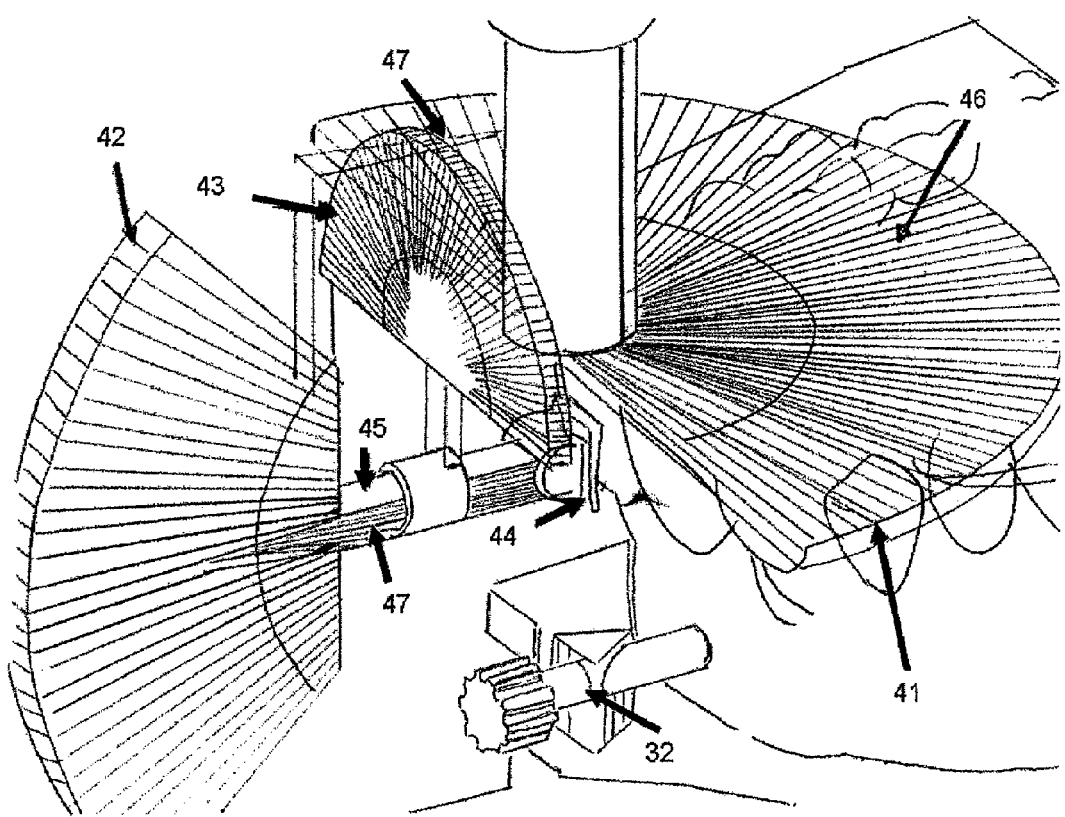

FIG. 7. It shows a close-up view of the precision position measuring accessory.

Figure 8A:
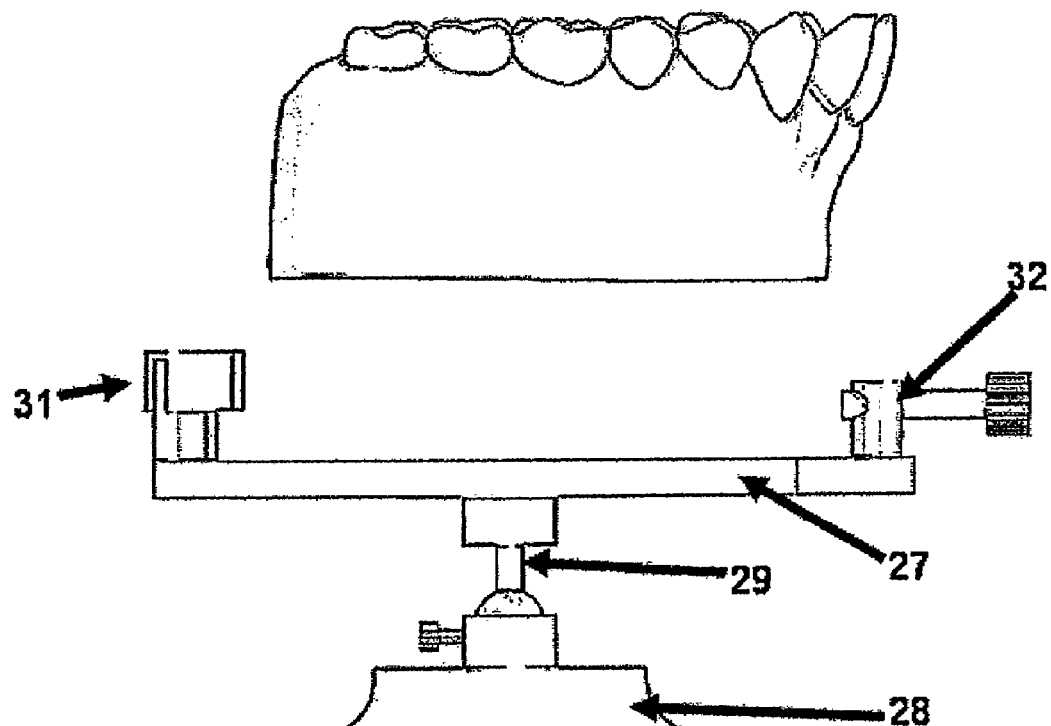
Figure 8B:
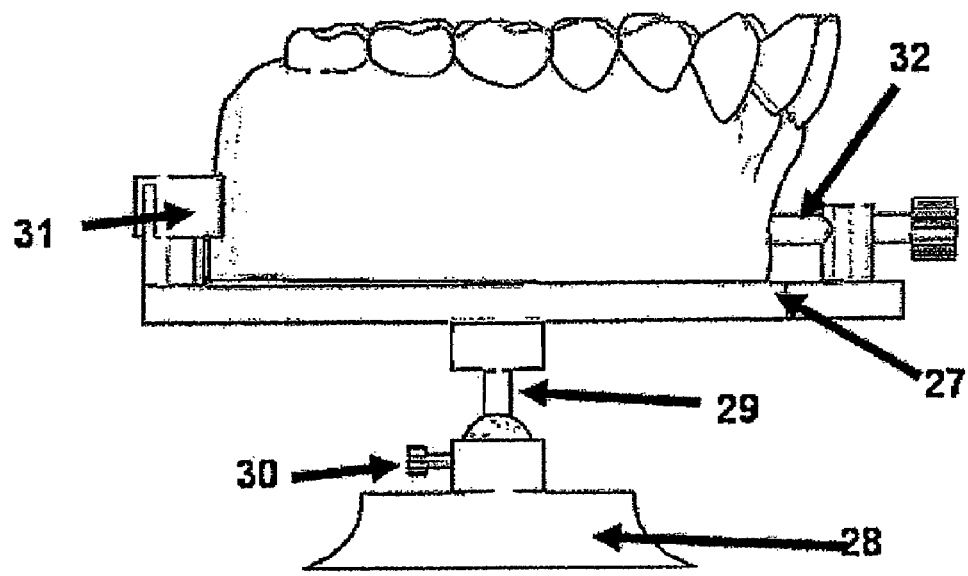

FIGS. 8A and 8B. They show the placement process of the dental cast on the support.

FIGS. 9A to 9D. They show the placement of the clear plate on the occlusal plane.

Figure 10A:
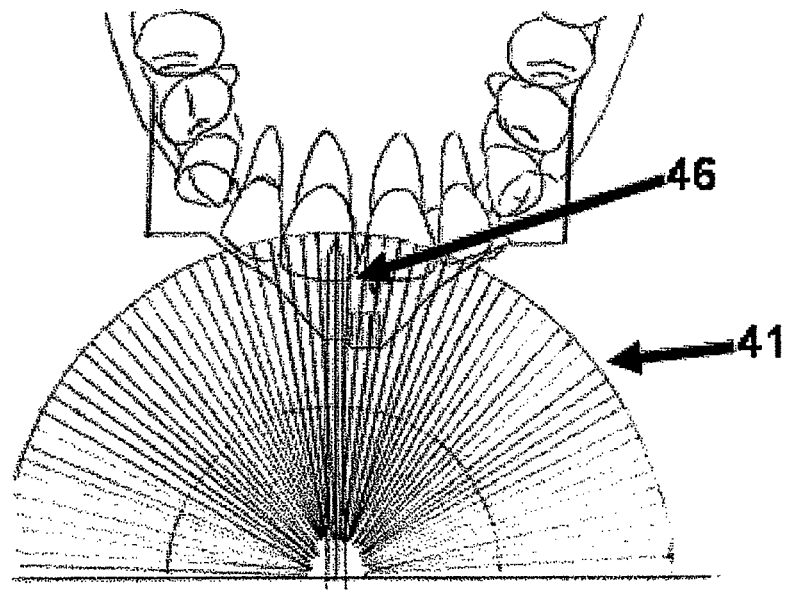
Figure 10B:
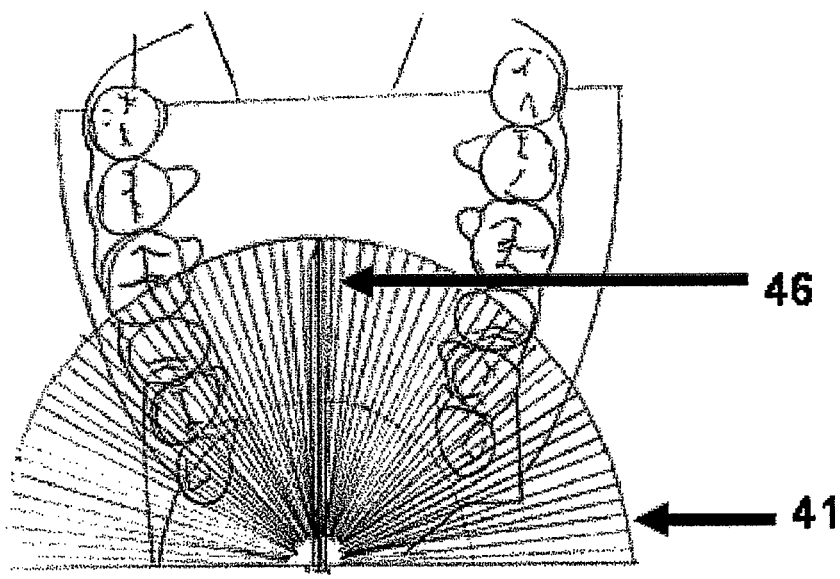

FIGS. 10A and 10B. They show the rotation record of the tooth

FIGS. 11A to 11D. They show the inclination and angulation recording of the tooth.

Figure 12A:
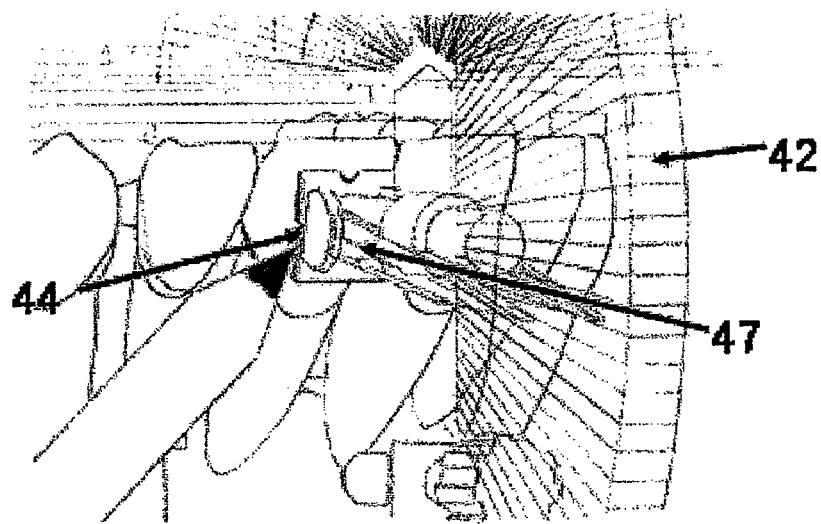
Figure 12B:
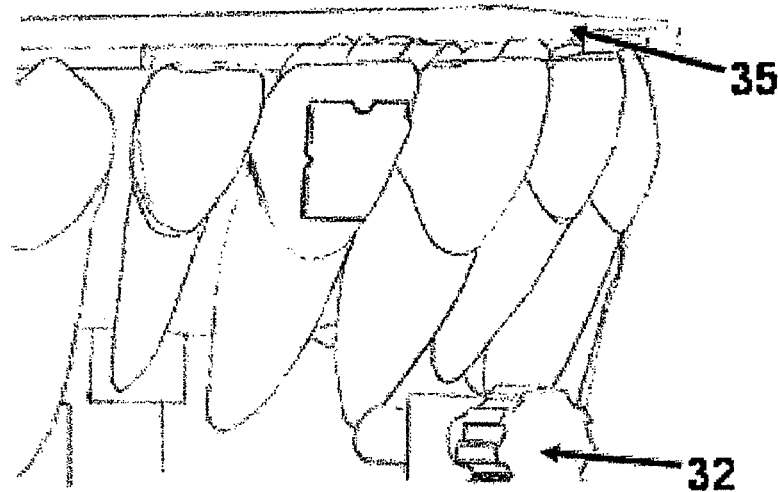

FIGS. 12A and 12B. They show the outlining of the tooth in the recording zone.

Figure 13A:
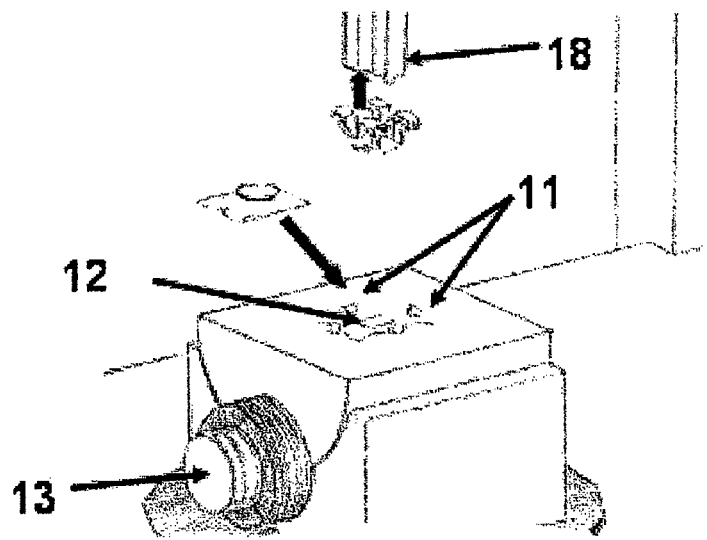
Figure 13B:
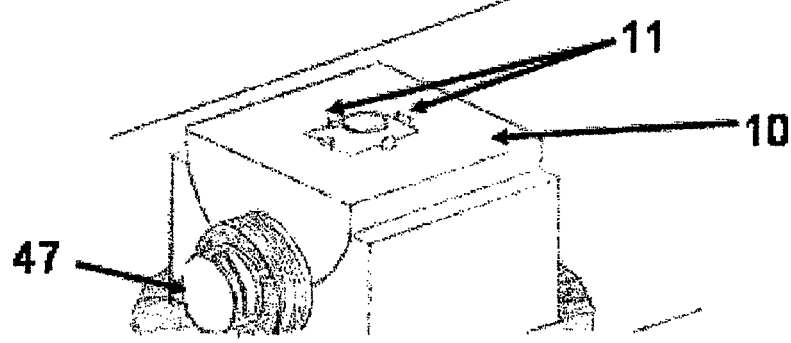

FIGS. 13A and 13B. They show the placement of the bracket elements on the welding accessory.

Figure 14A:
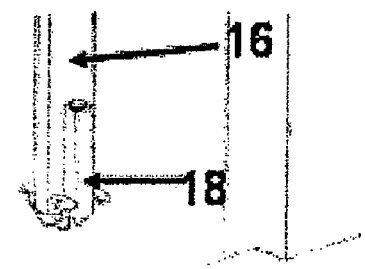
Figure 14B:
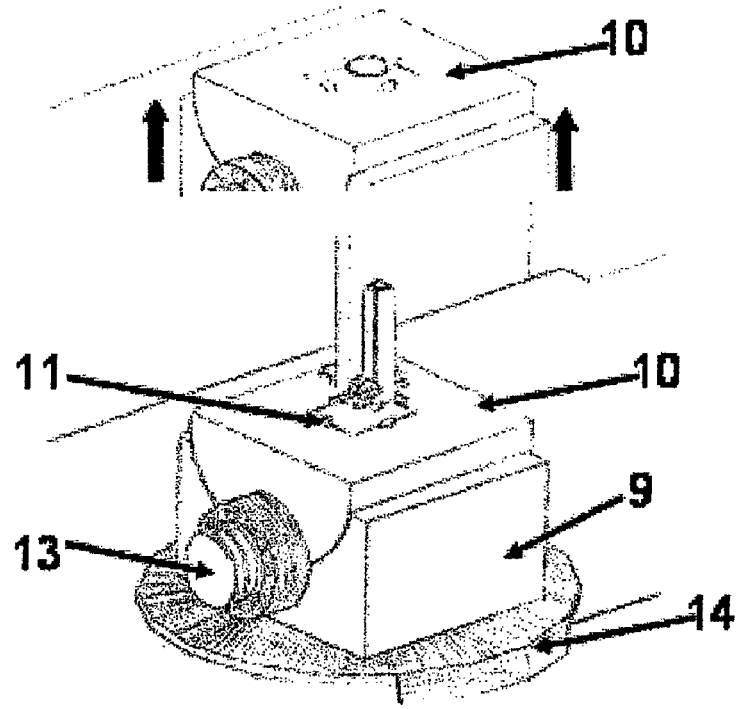

FIGS. 14A and 14B. They show the coupling of the welding electrodes.

Figure 15A:
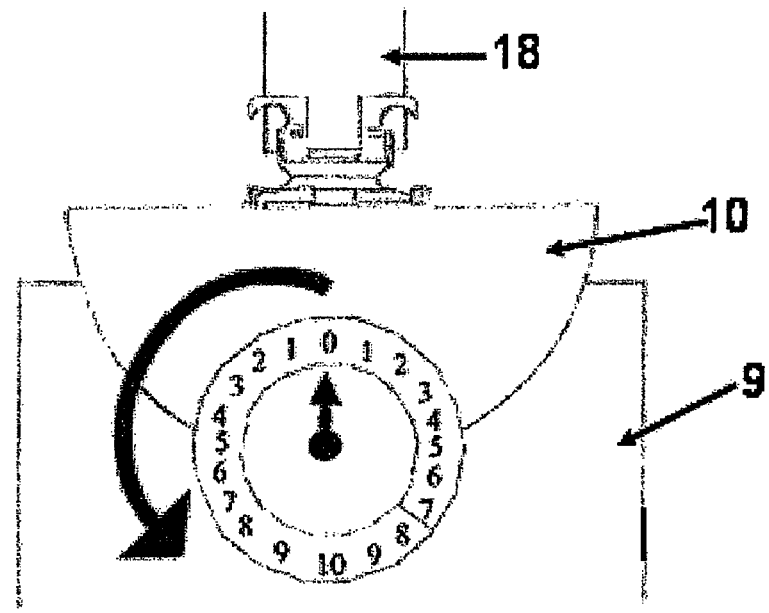
Figure 15B:
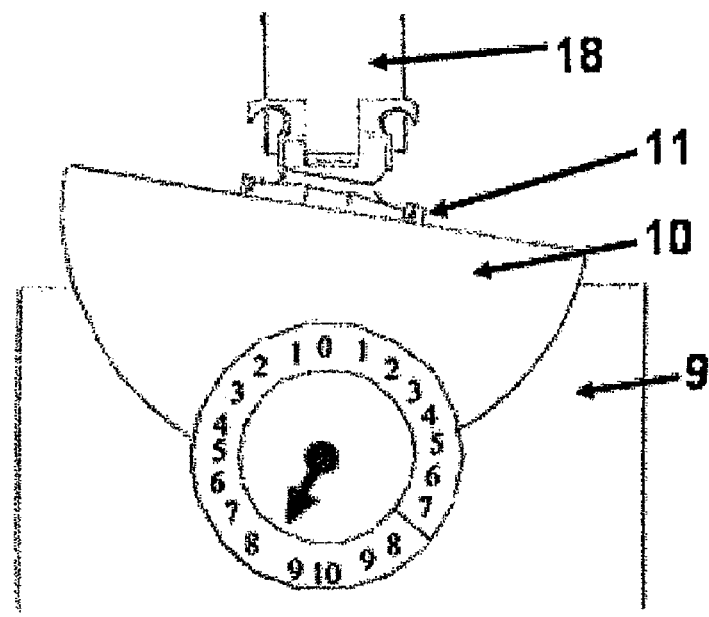

FIGS. 15A and 15B. They show the inclination programming.

Figure 16A:
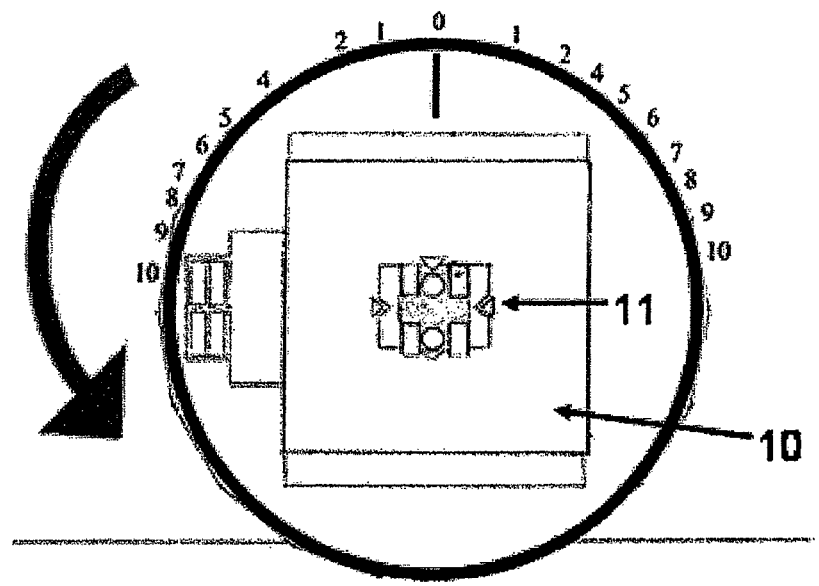
Figure 16B:
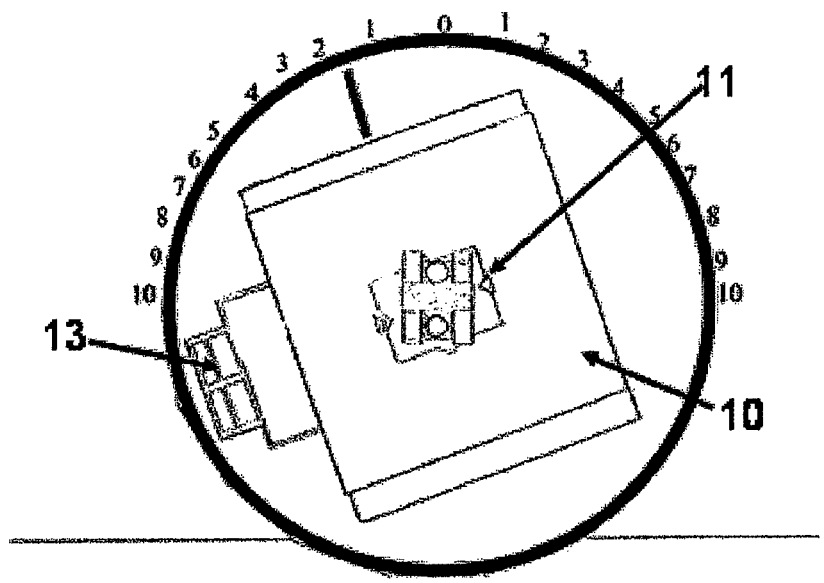

FIGS. 16A and 16B. They show the angulation programming.

Figure 17A:
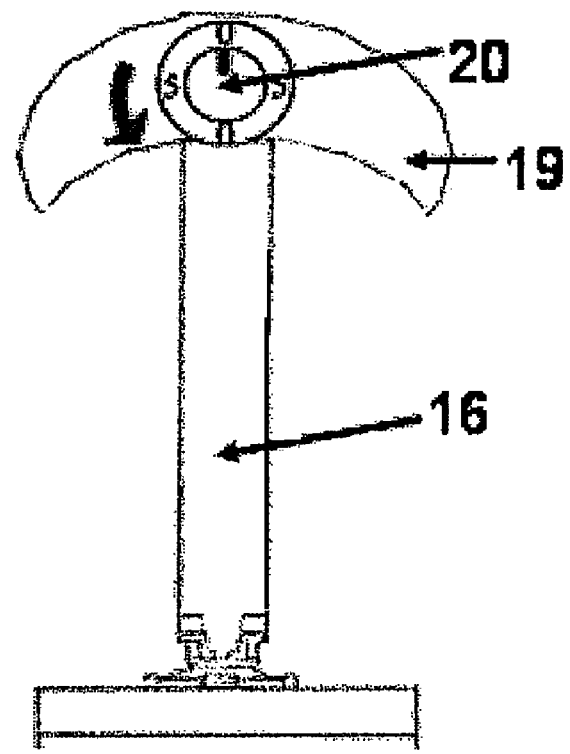
Figure 17B:
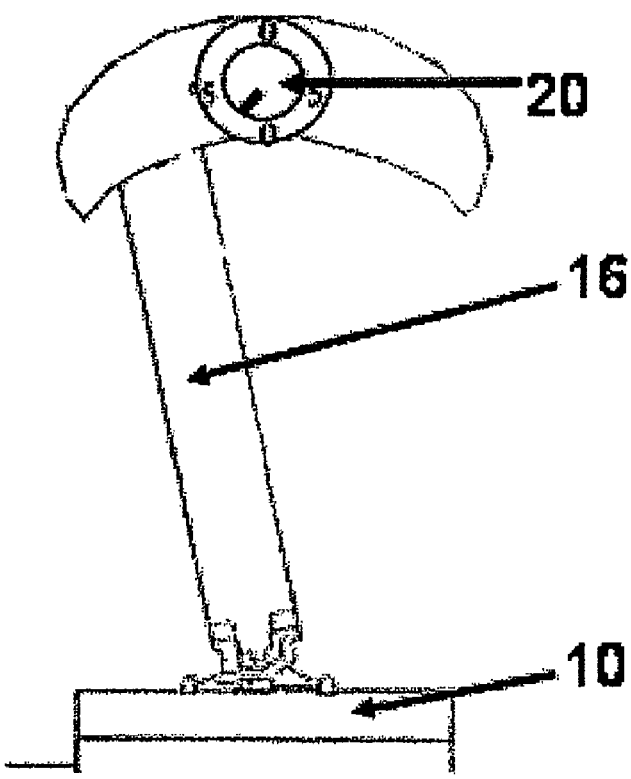

FIGS. 17A and 17B. They show the rotation programming.

WELDING ACCESSORY

It shows an on-off switch (1), which drives an on-pilot-led (2). There is a voltage selector or potentiometer (3), which regulates the electrical spot welding intensity or tempering in five intensities. It shows a switch (4) regulating the electrical spot welding or tempering duration, and a welding pilot-led (5). It shows a tempering switch (6) which drives a spot welding pilot-led (7) (FIG. 1).

The platform (8) displays vertical movement driven by an inner spring mechanism. Its central part has a support (9) with a table (10), and metallic guides (11) on which the bracket base is placed allowing the accurate positioning and adjustment of the bracket base on the table. This table also shows a rectangular-shaped copper point where the bracket base is coupled in order to perform welding (12) (FIGS. 1, 2, 13A, and 13B).

The support has a degree-graduated micrometric screw (13) which induces a movement in the antero-posterior sense on the table, that is to say, the table may be inclined in a tilting motion, one end upwards and the other end downwards, and in this way the bracket inclination may be programmed. The micrometric screw graduation ranges from −10° to +10°, with possible variations (FIGS. 2 and 3).

The platform shows a second micrometric screw (14), which induces a rotation movement of the support (9); that is to say, it may rotate clockwise or counter-clockwise. This micrometric screw has a graduation in degrees from −10° to +10°, with possible variations. This motion allows the bracket angulation to be programmed (FIG. 3).

The upper tower (15) has a copper rod (16) with a rounded-shaped double fine-point (17), displaying an interchangeable ceramic attachment that covers the rod. This rod introduced accurately in the slot receptacle of the bracket body (18), in this way the base-body coupling is achieved for its precision welding. The rod displays a crescent-shaped base (19) providing movement in the lateral sense modulated by means of a degree-graduated micrometric screw (20) which ranges from −10° to +10°, with possible variations. This function allows the bracket rotation to be programmed (FIGS. 3 and 4).

The fuse holder (21) contains the fuse aimed at protecting against voltage variation or possible current short circuit (FIG. 1).

The appliance displays a set of temperers (22) for the thermal treatment of the archwires (FIGS. 1 and 2).

The appliance has a power supply cord with a polarized plug which is plugged into an AC power source (23).

The current passage is regulated by a multiple transformer made up by a primary of 110 volts (24) and a multiple secondary (25) used at a 50-60 Hertz frequency at 10 amperes.

The transformer is parallel connected to the supports of both copper points, that of the platform (12) and that of the rod (17) and toward the set of two temperers (22). This transformer includes 5 intensities in the secondary, straightly directed to the potentiometer (3), from which a connection or port is obtained and directed to a copper terminal and to one of the temperers.

The second component of the parallel circuit is made up by the ground or common (26) where a port is originated connecting to the other copper terminal and to the remaining temperer, therefore having an open circuit between both copper terminals and both temperers (FIG. 5).

Principles of the Electrical Spot Welding Section

In electrical spot welding, the electrical current passes across two copper point electrodes; because of the resistance, the joining of the material is achieved by means of heat (temperatures of about 1000° C.), and the exertion of pressure on the parts that are going to be welded, thus generating a spot of welding.

The principle of the electrical spot welding machine is based on the passage of an electrical current through a conductor (in this case the base and the body of the bracket, manufactured in stainless steel) between two copper poles, causing a short-circuit controlled by a potentiometer.

The electrical spot welding is based on pressure and temperature. Two pieces are welded to each other when a part of them is heated to temperatures close to the fusion point and pressure is exerted over them. In this kind of welding the heating of the piece is achieved by means of an electrical current between two electrodes and the pressure is exerted just by both electrodes.

The aim of the electrodes is to pass the current across the bracket components that are going to be welded, and additionally to lock and press them together. The electrodes must be isolated from each other in such a way that the points are aligned. They are connected to the secondary coil of the transformer. The electrodes are manufactured in copper; the upper electrode is a double point that couples to the bracket body; both electrodes are cylindrical in shape. The lower electrode, coupling to the bracket base, has a rectangular shape. The double upper electrode has an interchangeable ceramic cover on its end which couples perfectly to the body of each bracket.

The electrode material is copper because compared to most metals copper has a lower electrical resistance and a higher thermal conductivity; this ensures that heat will be generated on the working part and not on the electrodes.

Before passing the electrical current, both bracket components (base and body) must be locked and pressed together, that is why the platform has a vertical motion driven by springs exerting pressure in order to achieve such an aim. If not so, the electrodes give off sparks and welding is no achieved. After performing some tests, one may decide to raise or lower the voltage by means of the potentiometer.

In order to prevent the generator from burning owing to excess current during its operation, the supplying transformer provides a maximal potency of the order of 1.5 kW, rather for a primary current of some 7 amperes. This is achieved by partially closing the magnetic circuit of the primary with soft iron plates, these plates may be observed just at the primary and secondary coils separation. The primary current has passed from 7 amperes to 18 amperes, with which theoretically the absorbed power is over 3.5 kW. This effect has been observed very noticeably, and with it the welding of stainless steel 1 mm thick has been achieved.

Materials Related to the Electrical Spot Welding

Steel allows the electrical spot welding and also the flame welding.

Stainless steel is the main alloy used in manufacturing orthodontic appliances such as wires, bands, attachments, tubes and brackets. It is constituted by the elements iron, carbon, nickel, and chrome.

The metals chrome and nickel are stabilized by forming stable oxides, so they prove to be adequate for making a metal resistant to oxidation. Austenitic steels (special intermetallic compounds of iron and carbon), on the addition of chrome and nickel, become non-oxidizable. These steels are the most resistant to corrosion, and specially the so-called 18-8, because it contains 18% chrome, 8% nickel and 0.15% carbon.

The steels utilized in orthodontics belong to the austenitic group, and mainly to the types AISI 302 and 304. Their typical composition contains, besides of iron, 17-19% of chrome, 8-10% nickel, up to 0.15% carbon, 2% manganese, 1% silicon and trace amounts of phosphor and sulphur. This typical composition undergoes different variations which make possible the existence of differences between the procedures of various manufacturers, and different kinds of steels are obtained according to their utility.

Nowadays we can find different alloys for the manufacture of brackets. By analyzing the bracket composition we find that silver, gold and nickel are the elements found in greater percentages for making up the alloys, and so the physical characteristics of these elements may have a strong influence on the welding process.

Formula for Calculating the Current Intensity

The electrical spot welding belongs to the family of the resistance welding. In order to generate heat, the copper electrodes pass an electrical current across the working piece; the generated heat will depend on the electrical resistance and the thermal conductivity of the metal, as well as the time of current application. Generated heat is represented by the following equation:

$$E = I \cdot R \cdot t$$

where E is the energy in the form of heat, I represents the electrical current, R represents the electrical resistance of the metal, and t is the time of current application.

In order to calculate the exact time of electrical spot welding, time must be found:

$$E/I \cdot R = t$$

In order to calculate the electrical current intensity, we have:

$$E/R \cdot t = I$$

Position Measuring Accessory

Figure 9A:
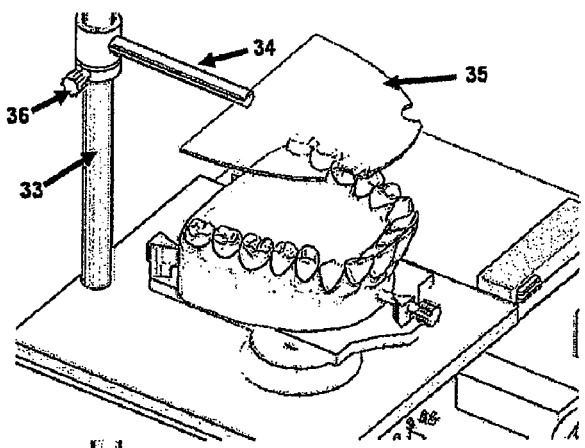
Figure 9B:
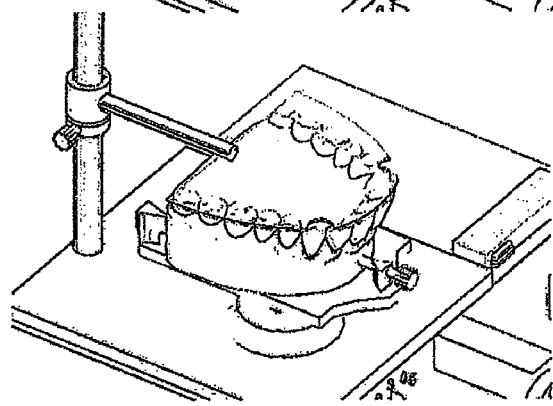
Figure 9C:
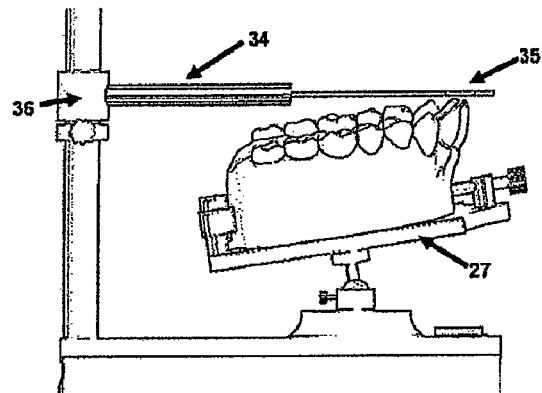
Figure 9D:
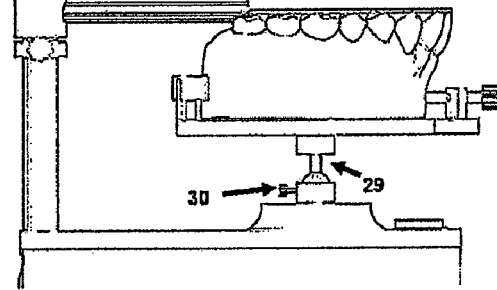

It shows a moveable metal platform (27) where the dental casts are placed; this platform is fastened to a base (28) by means of a connector (29) regulated by a fastening screw (30). The connector has a spherical end which joins to the place for that purpose in the base, and on the other end it has a thread for screwing to the platform (27) or directly to dental casts having the mounting plate of the articulator. The platform or dental cast inclination may be modified, which allows orienting the dental cast in such a way that the occlusal plane is parallel to the horizontal plane (FIGS. 6, 9A, and 9B).

The platform has metallic indentations (31) to fasten the dental cast and an anterior screw for the same purpose (32) (FIGS. 8A and 8B).

The attachment displays a fixed posterior rounded metal post (33) with two supports, a lower one and an upper one.

The lower support (34) holds up a clear acrylic plate (35) that can perform a vertical sliding movement along the post, in order to fit to the dental cast occlusal plane. The plate position may be fixed at the desired height by means of a fastening screw (36) (FIG. 6).

The upper support of the post (37) has an adjusting screw in the post permitting it to regulate its height (38), and on its end it has a metallic rod in vertical position (39) which has sliding motion regulated by an height adjusting screw (40). In its lower end this rod holds three acrylic degree-graduated recording templates, oriented in the three space planes (41, 42, and 43). It shows an interchangeable plastic bracket base (44), which fits to the labial face of the tooth that is going to be measured; this base represents the measurement surface and it is articulated to a plastic point (45), which in turn articulates to the recording needles of each template, thus its mechanism allows it to record the space position of the tooth face on the graduated templates (FIGS. 6 and 7).

The horizontal graduated template (41) allows orienting the tooth that is going to be measured at 90° in relation to its transversal axis, and thereafter to determine its inclination and angulation. This position would be equivalent to 0° rotation, being able to rotate the tooth according to the convenience of the case.

It shows a moveable needle indicating the degrees of rotation (46) (FIGS. 10A and 10B).

The sagital vertical template (42) indicates the inclination presented by the bracket base when it is placed on the tooth face; this template shows a needle indicating the degrees of inclination, ranging from +15° to −15° (47) (FIGS. 11A to 11D).

Figure 11A:
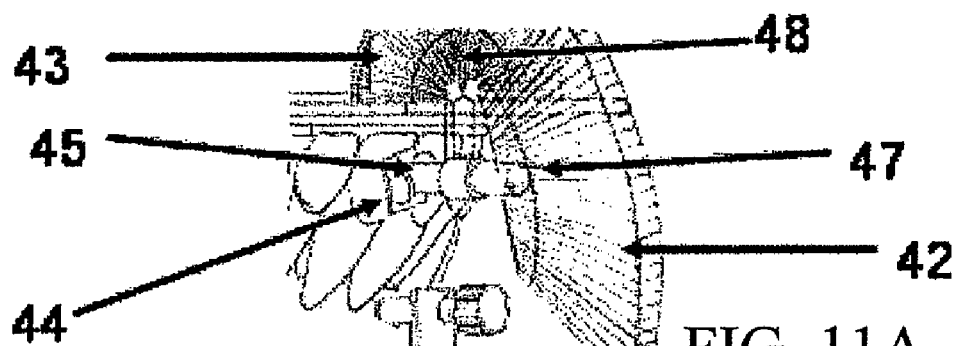
Figure 11B:
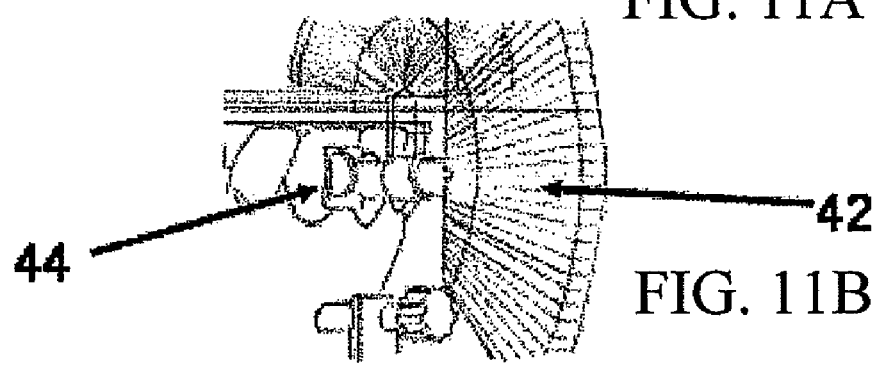
Figure 11C:
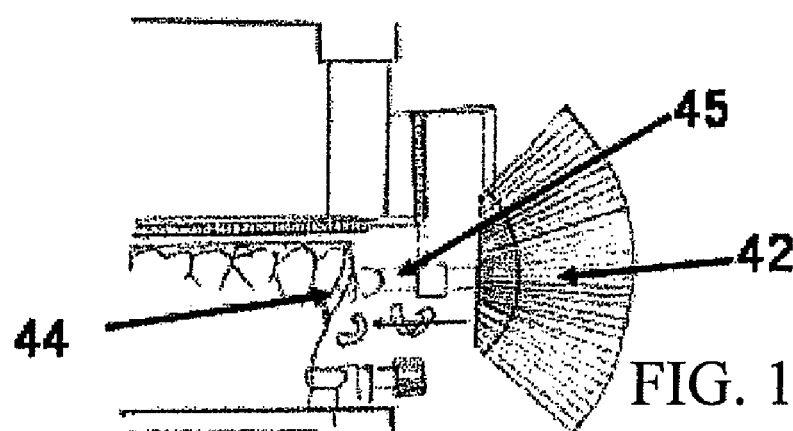
Figure 11D:
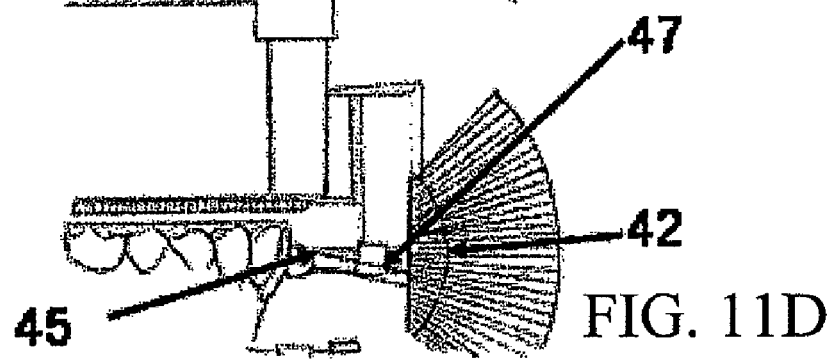

The graduated transverse vertical template (43) records the bracket base angulation when the base is adapted to the tooth labial face. This template shows an indicating needle with a range between +15° and −15° (48) (FIGS. 6, 7 and 11A).

USING THE INVENTION

THE MEASURING APPARATUS FOR PROGRAMMING AND WELDING OF ADJUSTABLE BRACKETS allows adjusting or programming the brackets in regard to the inclination, angulation and rotation that the orthodontist decides to incorporate in the brackets according to the clinical case own characteristics.

The following steps are suggested for the individualized programming of the bracket in regard to inclination, angulation and rotation.

1. Elaborate a set-up with the projection of how the completed case would be. It is important that this set-up is elaborated on dental casts mounted in centric relation in an adjustable or semi-adjustable articulator.

2. The dental casts with the teeth already positioned with the desired occlusion at the treatment completion are placed in the POSITION MEASUREMENT ACCESSORY; the plate used for mounting the dental cast on the articulator may be directly screwed down to the connector of the POSITION MEASUREMENT ACCESSORY, or the platform may be used with the rods and the dental cast fastening screw (FIG. 8).

3. Place the clear plate on the occlusal plane of the dental cast in order to parallelize it with the horizontal plane; note the plate shows relief zones for the canine cusp release (FIG. 9).

4. The dental cast must be oriented at 0° in relation to the horizontal template recording rotation. The clinician will determine if he wants to program anti-rotation (FIG. 10).

5. Perform a recording mapping of the tooth positions in regard to inclination, angulation. For that purpose, the plastic base of the bracket is placed on the labial face of the tooth that is going to be measured, the desired height is adjusted, and the system articulated to the plastic bracket base will measure the tooth inclination and angulation on the corresponding templates.

6. By means of a fine-pointed pencil, mark the contour of the plastic bracket base on the labial face of the tooth (FIG. 12).

7. Once the record mapping has been performed, proceed to weld the base and the body of the bracket in the WELDING ACCESSORY according to the previously obtained measurements.

8. Place the bracket base on the welding table, which has indentations for the proper placement (FIG. 13).

9. Proceed to couple the bracket body to the bracket base; for this purpose the interchangeable ceramic point suitable for the bracket that is going to be welded, which perfectly fits to the wings in the bracket body, is used (FIG. 14).

10. Proceed to program the desired inclination by means of the micrometric screw which moves the welding table in the anteroposterior sense, the micrometric screw graduation ranges from −10° to +10°, with possible variations (FIG. 15).

11. Proceed to program the desired angulation rotating clockwise or counterclockwise the micrometric screw which moves the platform where the welding table is located; the graduation of the micrometric screw ranges from −10° to +10°, with possible variations (FIG. 16).

12. Proceed to program the desired rotation by means of the micrometric screw which moves the welding rod in the lateral sense; the graduation of the micrometric screw ranges between −10° and +10°, with possible variations (FIG. 17).

13. Proceed to the electrical spot welding of the base and the body of the bracket.

14. Once the bracket is welded, proceed to fix it on the corresponding tooth in the dental cast, on the pencil-outlined zone previously described, for its subsequent placement in the mouth with the conventional indirect technique of bracket bonding.

Having described my invention sufficiently, I consider it a novelty with great usefulness and therefore I claim as my exclusive property, what is described below:

1. Measuring apparatus for the programming and welding of adjustable brackets characterized by including a position measuring system for dental casts and a welding system for dental brackets; where the position measuring system allows the measurement in dental casts of the tooth inclination, angulation and rotation position, transmitting this information to the adjustable brackets by means of the welding system; with the position measuring system includes: a connector where the dental casts can be placed, a ball-and-socket mechanism to modify the dental cast inclination, orienting it in such a way that the occlusal plane is parallel to the horizontal plane; a lower support holding up an angular tridimensional measurement system that permits to measure the inclination, angulation and rotation position of the teeth in the dental cast by means of a measurement surface adjustable to the labial face of each tooth that is going to be measured; and the welding system for performing the joining of an adjustable bracket of two pieces weldable to each other; this welding system comprises: an angular tridimensional measuring system which allows to adjust or program the inclination, angulation and rotation information obtained by the measuring system in order to be transmitted to the adjustable bracket; a lower support including a first electrode; an upper tower comprising a second electrode; the first and second electrodes form an electrical spot welding circuit; that lower support includes an attachment for introducing one part of the adjustable bracket and the upper tower has a mean to support the other part, so that the coupling of the adjustable bracket parts is achieved in order to weld them.

2. Measuring apparatus for the programming and welding of adjustable brackets according to claim 1, characterized by the angular tridimensional system of the measuring attachment comprising three goniometers or degree-graduated recording templates, oriented in the three space planes, receiving the information about the location of the measurement surface placed on the labial face of the teeth, in order to record the angulation, inclination and rotation measurements of the tooth clinical crowns and in this way to determine their accurate position.

3. Measuring apparatus for the programming and welding of adjustable brackets according to claim 1, characterized by the angular tridimensional measuring system of the welding system, it comprises three goniometers to register the movements in the three space planes.

4. Measuring apparatus for the programming and welding of adjustable brackets according to claim 3, characterized by the goniometers of the welding attachment being included by a first micrometric screw inducing movement in the table in the anteroposterior sense, that is to say, may be inclined in tilting motion: one end moves upwards and the other end moves downwards in order to program the bracket inclination; a second micrometric screw inducing rotation movement in the platform, that is to say, it can rotate clockwise or counterclockwise, for the programming of the bracket angulation; the rod comprises a crescent-shaped base for movement in lateral sense, modulated by a third micrometric screw, for the programming of the bracket rotation.

5. Measuring apparatus for the programming and welding of adjustable brackets according to claim 1, characterized by the connector joining to a moveable platform with metallic indentations and a fastening screw to fasten the dental cast.

6. Measuring apparatus for the programming and welding of adjustable brackets according to claim 4, characterized by the connector joining to the fastening screw in order to place dental casts with a mounting plate of the articulator directly screwing the mounting plate of the articulator to that fastening screw.

7. Measuring apparatus for the programming and welding of adjustable brackets according to claim 1, characterized by the measurement surface being the bracket base.

8. Method for measuring the programming and welding of adjustable brackets which allows to program the brackets in the inclination, angulation and rotation that the orthodontist decides to incorporate in the brackets according to the clinical case features; characterized by including the following steps:

a. provide a measuring apparatus for the programming and welding of adjustable brackets according to claim 1 and a set of adjustable brackets consisting in two weldable pieces;
  b. elaborate a dental cast (orthodontic set-up) with the projection of how the teeth will be at the treatment completion;
  c. mount the dental cast in the position measuring system in the connector of this system and orienting the dental cast in order to parallelize its occlusal plane with the horizontal plane;
  d. measure the inclination, angulation and rotation position of each tooth in the dental cast with the angular tridimensional measuring system by means of the measurement surface which is placed at a desired height and angulation on the labial face in the model of the tooth that is going to be measured, performing a record mapping of its position to provide the information about the clinical crown position of the tooth that is going to be measured in regard to inclination, angulation and rotation;
  e. mark the measurement surface contour over the labial face of the tooth;
  f. start the welding phase of both parts of an adjustable bracket, placing the bracket base on the first electrode in the welding system;
  g. couple the bracket body with the bracket base;
  h. adjust or program the inclination, angulation and rotation information of the dental cast obtained with the measuring system by using an angular tridimensional measuring system comprised in the welding system;
  i. proceed to the electrical spot welding of the base and the body of the bracket by means of the second electrode when in makes contact with the first electrode of the welding system;
  j. repeat the steps from d) to i) for every tooth in the dental cast;
  k. once the bracket is welded, proceed to fix it on the corresponding tooth in the dental cast over the outlined zone of the measurement surface of the bracket on the labial face of the tooth as it performed in step e).

9. Method for measuring the programming and welding of adjustable brackets which allows to program the brackets in the inclination, angulation and rotation that the orthodontist decides to incorporate in the brackets according to the clinical case features; characterized by including the following steps:

a. provide a measuring apparatus for the programming and welding of adjustable brackets according to claim 2 and a set of adjustable brackets consisting in two weldable pieces;
  b. elaborate a dental cast (orthodontic set-up) with the projection of how the teeth will be at the treatment completion;
  c. mount the dental cast in the position measuring system in the connector of this system and orienting the dental cast in order to parallelize its occlusal plane with the horizontal plane;
  d. measure the inclination, angulation and rotation position of each tooth in the dental cast with the angular tridimensional measuring system by means of the measurement surface which is placed at a desired height and angulation on the labial face in the model of the tooth that is going to be measured, performing a record mapping of its position to provide the information about the clinical crown position of the tooth that is going to be measured in regard to inclination, angulation and rotation;

e. mark the measurement surface contour over the labial face of the tooth;

f. start the welding phase of both parts of an adjustable bracket, placing the bracket base on the first electrode in the welding system;

g. couple the bracket body with the bracket base;

h. adjust or program the inclination, angulation and rotation information of the dental cast obtained with the measuring system by using an angular tridimensional measuring system comprised in the welding system;

i. proceed to the electrical spot welding of the base and the body of the bracket by means of the second electrode when in makes contact with the first electrode of the welding system;

j. repeat the steps from d) to i) for every tooth in the dental cast;

k. once the bracket is welded, proceed to fix it on the corresponding tooth in the dental cast over the outlined zone of the measurement surface of the bracket on the labial face of the tooth as it performed in step e).

10. Method for measuring the programming and welding of adjustable brackets which allows to program the brackets in the inclination, angulation and rotation that the orthodontist decides to incorporate in the brackets according to the clinical case features; characterized by including the following steps:

a. provide a measuring apparatus for the programming and welding of adjustable brackets according to claim 3 and a set of adjustable brackets consisting in two weldable pieces;

b. elaborate a dental cast (orthodontic set-up) with the projection of how the teeth will be at the treatment completion;

c. mount the dental cast in the position measuring system in the connector of this system and orienting the dental cast in order to parallelize its occlusal plane with the horizontal plane;

d. measure the inclination, angulation and rotation position of each tooth in the dental cast with the angular tridimensional measuring system by means of the measurement surface which is placed at a desired height and angulation on the labial face in the model of the tooth that is going to be measured, performing a record mapping of its position to provide the information about the clinical crown position of the tooth that is going to be measured in regard to inclination, angulation and rotation;

e. mark the measurement surface contour over the labial face of the tooth;

f. start the welding phase of both parts of an adjustable bracket, placing the bracket base on the first electrode in the welding system;

g. couple the bracket body with the bracket base;

h. adjust or program the inclination, angulation and rotation information of the dental cast obtained with the measuring system by using an angular tridimensional measuring system comprised in the welding system;

i. proceed to the electrical spot welding of the base and the body of the bracket by means of the second electrode when in makes contact with the first electrode of the welding system;

j. repeat the steps from d) to i) for every tooth in the dental cast;

k. once the bracket is welded, proceed to fix it on the corresponding tooth in the dental cast over the outlined zone of the measurement surface of the bracket on the labial face of the tooth as it performed in step e).

11. Method for measuring the programming and welding of adjustable brackets which allows to program the brackets in the inclination, angulation and rotation that the orthodontist decides to incorporate in the brackets according to the clinical case features; characterized by including the following steps:

a. provide a measuring apparatus for the programming and welding of adjustable brackets according to claim 4 and a set of adjustable brackets consisting in two weldable pieces;

b. elaborate a dental cast (orthodontic set-up) with the projection of how the teeth will be at the treatment completion;

c. mount the dental cast in the position measuring system in the connector of this system and orienting the dental cast in order to parallelize its occlusal plane with the horizontal plane;

d. measure the inclination, angulation and rotation position of each tooth in the dental cast with the angular tridimensional measuring system by means of the measurement surface which is placed at a desired height and angulation on the labial face in the model of the tooth that is going to be measured, performing a record mapping of its position to provide the information about the clinical crown position of the tooth that is going to be measured in regard to inclination, angulation and rotation;

e. mark the measurement surface contour over the labial face of the tooth;

f. start the welding phase of both parts of an adjustable bracket, placing the bracket base on the first electrode in the welding system;

g. couple the bracket body with the bracket base;

h. adjust or program the inclination, angulation and rotation information of the dental cast obtained with the measuring system by using an angular tridimensional measuring system comprised in the welding system;

i. proceed to the electrical spot welding of the base and the body of the bracket by means of the second electrode when in makes contact with the first electrode of the welding system;

j. repeat the steps from d) to i) for every tooth in the dental cast;

k. once the bracket is welded, proceed to fix it on the corresponding tooth in the dental cast over the outlined zone of the measurement surface of the bracket on the labial face of the tooth as it performed in step e).

12. Method for measuring the programming and welding of adjustable brackets which allows to program the brackets in the inclination, angulation and rotation that the orthodontist decides to incorporate in the brackets according to the clinical case features; characterized by including the following steps:

a. provide a measuring apparatus for the programming and welding of adjustable brackets according to claim 5 and a set of adjustable brackets consisting in two weldable pieces;

b. elaborate a dental cast (orthodontic set-up) with the projection of how the teeth will be at the treatment completion;

c. mount the dental cast in the position measuring system in the connector of this system and orienting the dental cast in order to parallelize its occlusal plane with the horizontal plane;
d. measure the inclination, angulation and rotation position of each tooth in the dental cast with the angular tridimensional measuring system by means of the measurement surface which is placed at a desired height and angulation on the labial face in the model of the tooth that is going to be measured, performing a record mapping of its position to provide the information about the clinical crown position of the tooth that is going to be measured in regard to inclination, angulation and rotation;
e. mark the measurement surface contour over the labial face of the tooth;
f. start the welding phase of both parts of an adjustable bracket, placing the bracket base on the first electrode in the welding system;
g. couple the bracket body with the bracket base;
h. adjust or program the inclination, angulation and rotation information of the dental cast obtained with the measuring system by using an angular tridimensional measuring system comprised in the welding system;
i. proceed to the electrical spot welding of the base and the body of the bracket by means of the second electrode when in makes contact with the first electrode of the welding system;
j. repeat the steps from d) to i) for every tooth in the dental cast;
k. once the bracket is welded, proceed to fix it on the corresponding tooth in the dental cast over the outlined zone of the measurement surface of the bracket on the labial face of the tooth as it performed in step e).

13. Method for measuring the programming and welding of adjustable brackets which allows to program the brackets in the inclination, angulation and rotation that the orthodontist decides to incorporate in the brackets according to the clinical case features; characterized by including the following steps:
a. provide a measuring apparatus for the programming and welding of adjustable brackets according to claim 6 and a set of adjustable brackets consisting in two weldable pieces;
b. elaborate a dental cast (orthodontic set-up) with the projection of how the teeth will be at the treatment completion;
c. mount the dental cast in the position measuring system in the connector of this system and orienting the dental cast in order to parallelize its occlusal plane with the horizontal plane;
d. measure the inclination, angulation and rotation position of each tooth in the dental cast with the angular tridimensional measuring system by means of the measurement surface which is placed at a desired height and angulation on the labial face in the model of the tooth that is going to be measured, performing a record mapping of its position to provide the information about the clinical crown position of the tooth that is going to be measured in regard to inclination, angulation and rotation;
e. mark the measurement surface contour over the labial face of the tooth;
f. start the welding phase of both parts of an adjustable bracket, placing the bracket base on the first electrode in the welding system;
g. couple the bracket body with the bracket base;
h. adjust or program the inclination, angulation and rotation information of the dental cast obtained with the measuring system by using an angular tridimensional measuring system comprised in the welding system;
i. proceed to the electrical spot welding of the base and the body of the bracket by means of the second electrode when in makes contact with the first electrode of the welding system;
j. repeat the steps from d) to i) for every tooth in the dental cast;
k. once the bracket is welded, proceed to fix it on the corresponding tooth in the dental cast over the outlined zone of the measurement surface of the bracket on the labial face of the tooth as it performed in step e).

14. Method for measuring the programming and welding of adjustable brackets which allows to program the brackets in the inclination, angulation and rotation that the orthodontist decides to incorporate in the brackets according to the clinical case features; characterized by including the following steps:
a. provide a measuring apparatus for the programming and welding of adjustable brackets according to claim 7 and a set of adjustable brackets consisting in two weldable pieces;
b. elaborate a dental cast (orthodontic set-up) with the projection of how the teeth will be at the treatment completion;
c. mount the dental cast in the position measuring system in the connector of this system and orienting the dental cast in order to parallelize its occlusal plane with the horizontal plane;
d. measure the inclination, angulation and rotation position of each tooth in the dental cast with the angular tridimensional measuring system by means of the measurement surface which is placed at a desired height and angulation on the labial face in the model of the tooth that is going to be measured, performing a record mapping of its position to provide the information about the clinical crown position of the tooth that is going to be measured in regard to inclination, angulation and rotation;
e. mark the measurement surface contour over the labial face of the tooth;
f. start the welding phase of both parts of an adjustable bracket, placing the bracket base on the first electrode in the welding system;
g. couple the bracket body with the bracket base;
h. adjust or program the inclination, angulation and rotation information of the dental cast obtained with the measuring system by using an angular tridimensional measuring system comprised in the welding system;
i. proceed to the electrical spot welding of the base and the body of the bracket by means of the second electrode when in makes contact with the first electrode of the welding system;
j. repeat the steps from d) to i) for every tooth in the dental cast;
k. once the bracket is welded, proceed to fix it on the corresponding tooth in the dental cast over the outlined zone of the measurement surface of the bracket on the labial face of the tooth as it performed in step e).

* * * * *